(12) United States Patent
Cheng et al.

(10) Patent No.: US 10,702,151 B2
(45) Date of Patent: Jul. 7, 2020

(54) FUNDUS CAMERA (71) Applicant: Medimaging Integrated Solution, Inc., Hsinchu (TW)

(72) Inventors: Chu-Ming Cheng, Hsinchu (TW); Long-Sheng Liao, Hsinchu (TW); Che-Jung Kuo, Tainan (TW); Wei-hsun Chang, Zhubei (TW)

(73) Assignee: Medimaging Integrated Solution, Inc., Hsinchu (TW)

(*) Notice: Subject to any disclaimer, the term of this patent is extended or adjusted under 35 U.S.C. 154(b) by 159 days.

(21) Appl. No.: 16/139,411

(22) Filed: Sep. 24, 2018

(65) Prior Publication Data

US 2020/0054210 A1 Feb. 20, 2020

(30) Foreign Application Priority Data

Aug. 14, 2018 (TW) .............................. 107128370 A (51) Int. Cl.
| | |
|---|---|
| *A61B 3/14* | (2006.01) |
| *A61B 3/12* | (2006.01) |
| *A61B 3/00* | (2006.01) |

(52) U.S. Cl.
CPC .............. *A61B 3/12* (2013.01); *A61B 3/0008* (2013.01); *A61B 3/0075* (2013.01)

(58) Field of Classification Search
CPC ....... A61B 3/113; A61B 3/0008; A61B 5/163; A61B 2017/00694; A61B 2017/00057; A61F 2009/00846; A61F 2009/00844; G01B 9/02068
USPC ................................ 351/206, 208, 209, 221
See application file for complete search history.

(56) References Cited

U.S. PATENT DOCUMENTS 4,443,075 A 4/1984 Crane

FOREIGN PATENT DOCUMENTS

| | | |
|---|---|---|
| CN | 105581771 B | 7/2017 |
| TW | I629045 B | 7/2018 |

*Primary Examiner* — Mahidere S Sahle
(74) *Attorney, Agent, or Firm* — Muncy, Geissler, Olds & Lowe, P.C.

(57) ABSTRACT

A fundus camera includes an eyeball-offset detection device and an annular illumination device. The eyeball-offset detection device is configured to detect an offset vector of a lens of the fundus camera relative to an inspected eyeball. The annular illumination device includes a plurality of illumination elements that are arranged in a ring shape around an optical axis of an imaging system of the fundus camera. According to the offset vector of the lens relative to the inspected eyeball, the fundus camera selectively activates one or more illumination elements at corresponding positions to keep an illumination optical path away from a center area of the pupil of the inspected eyeball to reduce effects of corneal reflection and improve illumination quality. Therefore, the abovementioned fundus camera has a large operable range.

18 Claims, 7 Drawing Sheets

FUNDUS CAMERA

BACKGROUND OF THE INVENTION

1. Field of the Invention

The present invention relates to a fundus camera, particularly to a fundus camera with an adaptive illumination light source.

2. Description of the Prior Art

In order to form images, a fundus camera must project illumination light through a pupil of an inspected eyeball to the fundus. The light reflected by the fundus also passes through the pupil of the inspected eyeball, processed by an imaging system to form images on the eyes of an observer or an image sensor (or a film). It is easy to understand: the other lights, such as the lights reflected by the cornea or iris, are stray lights for the imaging system. Therefore, separation of the illumination optical path and the imaging optical path is favorable for imaging quality.

Figure 1A:
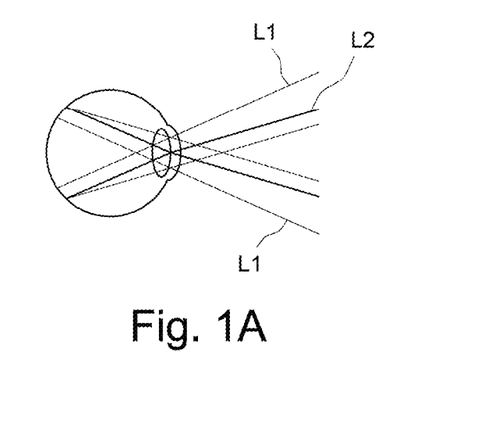
FIG. 1A is a diagram schematically showing illumination optical paths and an imaging optical path of a conventional fundus camera using an annular illumination design, wherein the illumination optical paths and the imaging optical path are observed at an direction vertical to an optical axis of a lens of the fundus camera.
Figure 1B:
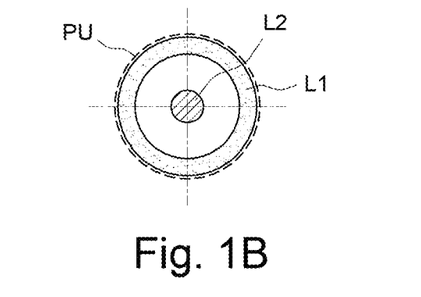
FIG. 1B is a diagram schematically showing the illumination optical path and the imaging optical path of a conventional fundus camera using an annular illumination design, wherein the illumination optical path and the imaging optical path are observed at a direction parallel to the optical axis of the lens of the fundus camera.

A conventional fundus camera adopts an annular type illumination design. In other words, the illumination light passes through the perimeter of the pupil to the fundus in form of a ring, and the imaging optical path passes through the central hollow region of the annular optical path to the imaging system. Refer to FIG. 1A and FIG. 1B diagrams schematically showing a pupil PU, an annular illumination optical path L1 and an imaging optical path L2. The annular type illumination design can increase uniformity of illumination on the fundus and decrease ghost images reflected by the cornea and iris. However, the annular illumination system needs a condenser lens, a light blocking baffle having an annular opening, a relay lens, and a reflective mirror having a circular opening, etc., which make the annular illumination system have a higher cost and a larger volume. Besides, assembling and adjusting the annular illumination system requires higher technology and consumes more time.

Figure 2A:
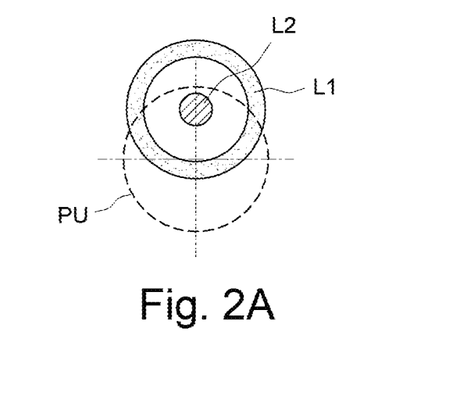
FIG. 2A and FIG. 2B are diagrams schematically showing the illumination optical path and the imaging optical path of a conventional fundus camera using an annular illumination design, wherein the illumination optical path and the imaging optical path are observed at a direction parallel to the optical axis of the lens of the fundus camera while the inspected eyeball is deviated.
Figure 2B:
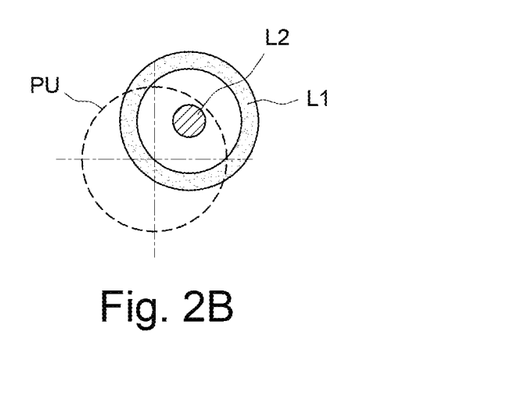

Refer to FIG. 2A and FIG. 2B. While the imaging optical path L2 is deviated with respect to the pupil PU in operation, the annular illumination optical path L1 is also deviated with respect to the pupil PU. In such a case, the annular illumination optical path will approach the central region of the cornea, which would generate unnecessary ghost images of the cornea. Therefore, the conventional fundus camera using an annular illumination design cannot achieve the imaging quality in the original design unless the lens is aligned to the pupil to a certain extent of accuracy. Thus, the operation of the conventional fundus camera is less convenient, or the operator needs more training.

Figure 3A:
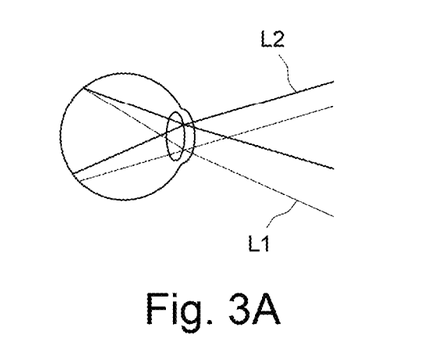
FIG. 3A is a diagram schematically showing an illumination optical path and an imaging optical path of a conventional fundus camera using a single-point illumination design, wherein the illumination optical path and the imaging optical path are observed at an direction vertical to an optical axis of the lens of the fundus camera.
Figure 3B:
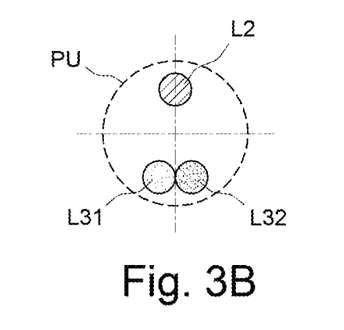
FIG. 3B is a diagram schematically showing the illumination optical paths and the imaging optical path of a conventional fundus camera using a single-point illumination design, wherein the illumination optical path and the imaging optical path are observed at an direction parallel to the optical axis of the lens of the fundus camera.
Figure 4A:
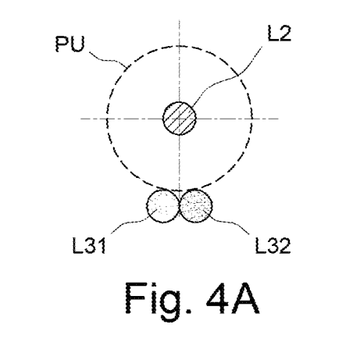
FIG. 4A and FIG. 4B are diagrams schematically showing the illumination optical paths and the imaging optical path of a conventional fundus camera using a single-point illumination design, wherein the illumination optical paths and the imaging optical path are observed at a direction parallel to the optical axis of the lens of the fundus camera while the inspected eyeball is deviated.
Figure 4B:
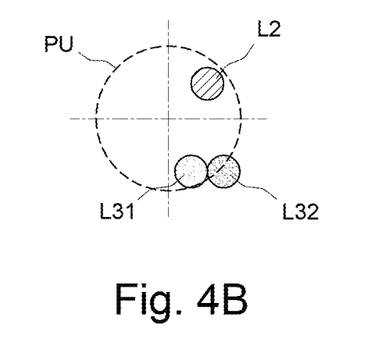

Another conventional fundus camera adopts an off-axis single-point illumination design. Refer to FIG. 3A and FIG. 3B diagrams schematically showing a pupil PU and an imaging optical path L2, and single-point illumination paths L31 and L32. For example, the single-point illumination path L31 may use infrared light, and the single-point illumination path L32 may use visible light. Compared with the annular illumination design, the single-point illumination design has a larger illumination angle and distributes light on all the fundus. The advantages of the single-point illumination design include low cost, simple structure, and small volume. However, refer to FIG. 4A and FIG. 4B, while the lens of the fundus camera is deviated with respect to the inspected eyeball, the imaging optical path L2 and single-point illumination paths L31 and L32 are less likely to pass through the pupil simultaneously, especially for the inspected eyeball with a smaller pupil. Thus, imaging is hard to complete, or the imaging quality is poor. Therefore, the conventional fundus camera using a single-point illumination design either cannot achieve the imaging quality in the original design unless the lens is aligned to the pupil to a certain extent of accuracy.

Accordingly, how to acquire fundus images with better quality while the lens deviates from the inspected eyeball has become an objective the manufactures are eager to achieve.

SUMMARY OF THE INVENTION

The present invention provides a fundus camera having a plurality of point-type light sources. According to the offset vector of the lens with respect to the inspected eyeball, the fundus camera selectively activates one or more point-type light sources at specified positions, whereby to provide appropriate illumination and acquire fundus images with better quality although the lens is deviated.

In one embodiment, the fundus camera of the present invention comprises a first lens group, an eyeball-offset detection device, an annular illumination device, a processor, a second lens group, an image sensor, and a display device. The first lens group has a first side and a second side opposite to the first side. The first side faces the inspected eyeball. The eyeball-offset detection device detects a relative position of the first lens group and the inspected eyeball. The annular illumination device is arranged between the first lens group and the second lens group and includes a plurality of illumination elements arranged annularly. An optical axis of the first lens group passes through the hollow region of the annular illumination device. The processor is electrically connected with the eyeball-offset detection device and the annular illumination device. The processor works out an offset vector according to the relative position of the first lens group and the inspected eyeball and selectively activates at least one of the plurality of illumination elements to generate an illumination light according to the offset vector. The illumination light passes through the first lens group to the fundus of the inspected eyeball, and the fundus reflects the illumination light to form an imaging light. The second lens group is coaxially arranged in the second side of the first lens group. The image sensor is arranged in a light exit side of the second lens group. The imaging light passes the first lens group and the second lens group and converges on the image sensor in sequence to form a fundus image. The display device is electrically connected with the image sensor and displays the fundus image formed in the image sensor.

Below, embodiments are described in detail in cooperation with the attached drawings to make easily understood the objectives, technical contents, characteristics and accomplishments of the present invention.

DESCRIPTION OF THE PREFERRED EMBODIMENTS

The present invention will be described in detail with embodiments and attached drawings below. However, these embodiments are only to exemplify the present invention but not to limit the scope of the present invention. In addition to the embodiments described in the specification, the present invention also applies to other embodiments. Further, any modification, variation, or substitution, which can be easily made by the persons skilled in that art according to the embodiment of the present invention, is to be also included within the scope of the present invention, which is based on the claims stated below. Although many special details are provided herein to make the readers more fully understand the present invention, the present invention can still be practiced under a condition that these special details are partially or completely omitted. Besides, the elements or steps, which are well known by the persons skilled in the art, are not described herein lest the present invention be limited unnecessarily. Similar or identical elements are denoted with similar or identical symbols in the drawings. It should be noted: the drawings are only to depict the present invention schematically but not to show the real dimensions or quantities of the present invention. Besides, matterless details are not necessarily depicted in the drawings to achieve conciseness of the drawings.

Figure 5:
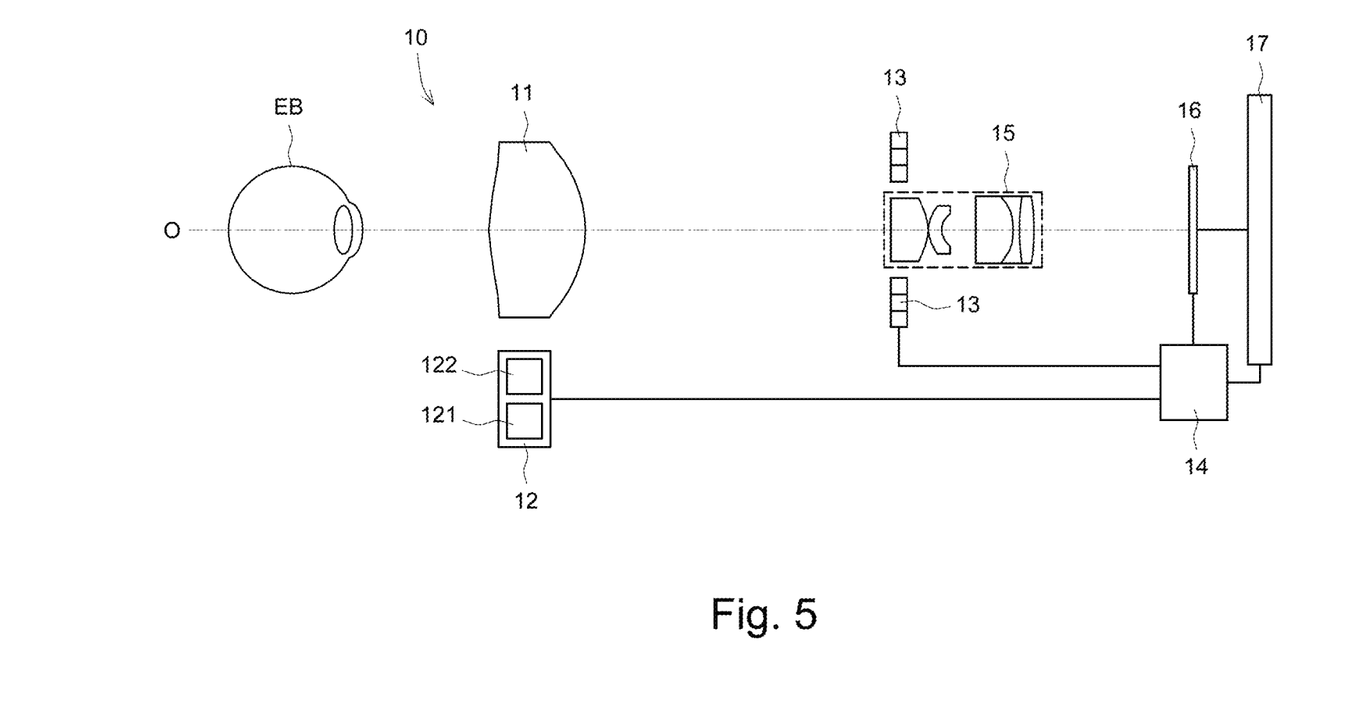
FIG. 5 is a diagram schematically showing a fundus camera according to one embodiment of the present invention.

Refer to FIG. 5. In one embodiment, the fundus camera 10 of the present invention comprises a first lens group 11, an eyeball-offset detection device 12, an annular illumination device 13, a processor 14, a second lens group 15, an image sensor 16, and a display device 17. The first lens group 11 has a first side and a second side opposite to the first side. The first side faces an inspected eyeball EB. In one embodiment, the first lens group 11 is composed of a single biconvex lens, whereby to prevent from ghost images generated by that the first lens group 11 reflects the illumination light to the second lens group 15.

The eyeball-offset detection device 12 detects a relative position of the first lens group 11 and the inspected eyeball EB. The processor 14 calculates the relative position of the first lens group 11 and the inspected eyeball EB to work out an offset vector between the eyeball EB and the first lens group 11. For example, the eyeball-offset detection device 12 includes an extraocular image sensor 121, which can capture the extraocular images of the inspected eyeball EB. According to the extraocular images captured by the eyeball-offset detection device 12, the processor 14 can work out the offset vector of the first lens group 11 with respect to the inspected eyeball EB, including the offset direction and the offset distance. In one embodiment, the eyeball-offset detection device 12 may be a stereo camera, which can capture at least two extraocular images from different positions in space; the processor 14 can work out the offset vector of the first lens group 11 with respect to the inspected eyeball EB according to two extraocular images captured by the stereo camera.

In one embodiment, the eyeball-offset detection device 12 further includes a reference illumination element 122, which generates a reference light to irradiate on the inspected eyeball EB. The reference light projected onto the inspected eyeball EB is reflected by the cornea. Via appropriate space configuration, the reference light reflected by the cornea is captured by the extraocular image sensor 121 to form a reference light spot on the extraocular images. It is easily understood: while the first lens group 11 is correctly aligned to the inspected eyeball EB, the reference light spot will appear in a given position of the extraocular image. While the first lens group 11 is deviated with respect to the inspected eyeball EB, the reference light spot will be offset from the given position of the extraocular image. According to a reference position of the reference light spot in the extraocular image, the processor can work out a more accurate offset vector. In one embodiment, the reference light emitted by the reference illumination element 122 is an invisible light, such as an infrared light, lest the pupil of the inspected eyeball EB constrict.

Figure 6A:
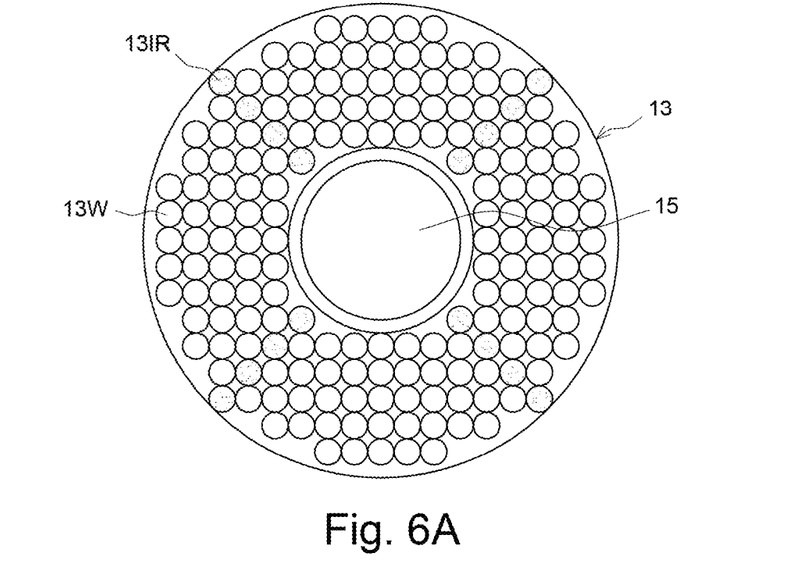
FIG. 6A, FIG. 6B, FIG. 7A, and FIG. 7B are diagrams schematically showing annular illumination devices of a fundus camera according to embodiments of the preset invention.
Figure 7A:
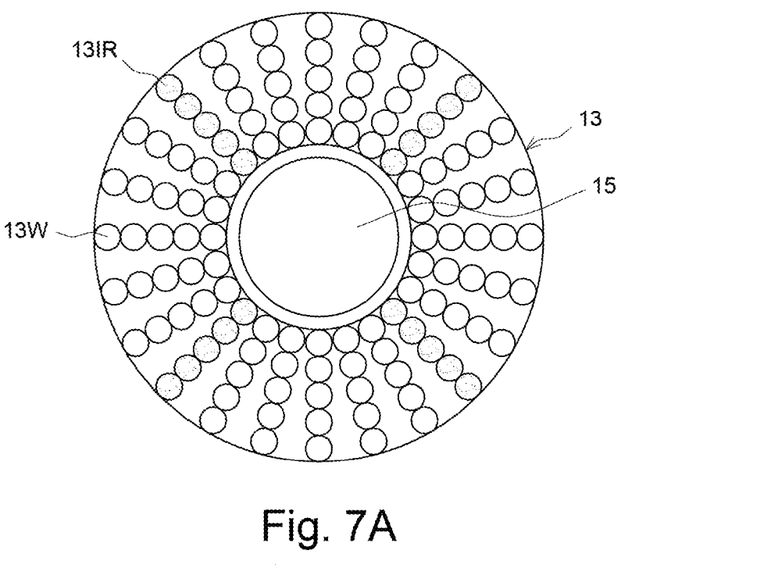

The annular illumination device 13 is arranged in the second side of the first lens group 11 and opposite to the inspected eyeball EB. An optical axis O of the first lens group 11 passes through a hollow region of the annular illumination device 13. In one embodiment, the optical axis O of the first lens group 11 passes through the geometrical center of the annular illumination device 13. The annular illumination device 13 includes a plurality of illumination elements annularly arranged. For example, with the optical axis of the first lens group 11 being the center, the plurality of illumination elements 13W and 13IR is arranged outwards in arrays, as shown in FIG. 6A, or the plurality of illumination elements 13W and 13IR is arranged outwards radiately, as shown in FIG. 7A. In one embodiment, with the optical axis O of the first lens group 11 being the center, the plurality of illumination elements is arranged outwards alternately. In one embodiment, the illumination elements 13IR may be point-type illumination elements, such as infrared light LEDs, providing illumination for observing the fundus before images are captured. In one embodiment, the illumination elements 13W may be point-type illumination elements, such as white light LEDs, providing illumination for capturing fundus images.

Figure 6B:
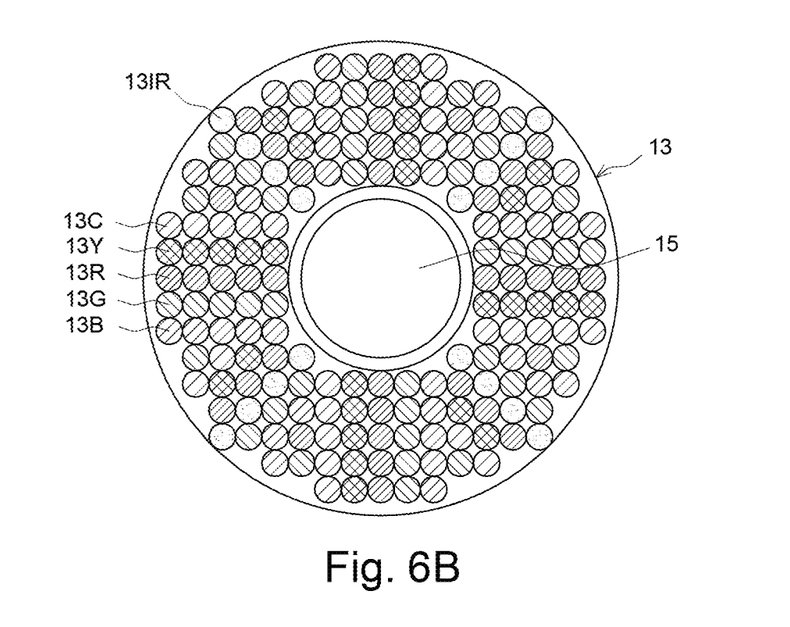
Figure 7B:
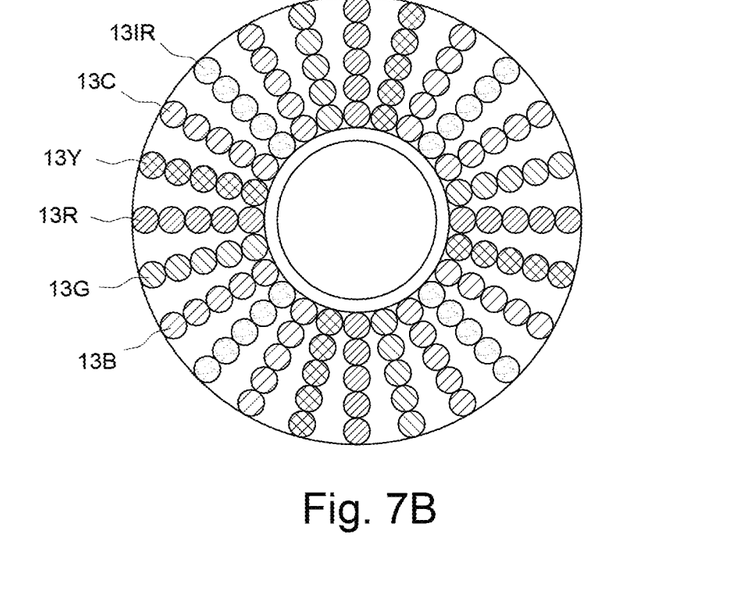

Refer to FIG. 6B and FIG. 7B. In one embodiment, the annular illumination device 13 includes a plurality of infrared light LEDs (such as the illumination elements 13IR) and a plurality of visible light LEDs respectively emitting visible lights of different wavelength bands (such as the illumination elements 13R, 13G, 13B, 13Y, and 13C). For example, the visible light LEDs respectively emitting visible lights of different wavelength bands may be red light LEDs, green light LEDs, blue light LEDs, yellow light LEDs, and cyan light LEDs. Different tissues respectively have different absorption spectra. Via collecting and combining different wavelength band signals respectively reflected from different tissues in different depths of the fundus, the acquired information can be used to verify whether there is any abnormality in the fundus. For example, green light is sensitive to blood vessels and used to verify whether there is hemorrhage in the fundus; yellow red light is useful in identifying the exudate of retinal pigment epithelium (such as drusen) and angiogenesis.

Refer to FIG. 5 and FIG. 6A or FIG. 7A. The processor 14 is electrically connected with the eyeball-offset detection device 12 and the annular illumination device 13. According to the offset vector of the first lens group 11 with respect to the inspected eyeball EB, the processor 14 selectively activates at least one of the plurality of illumination elements 13IR and 13W to generate an illumination light. The illumination light is not reflected but directly projected onto the first lens group 11. The first lens group 11 converges the illumination light and projects the illumination light onto the fundus. The fundus of the inspected eyeball EB reflects the illumination light to form an imaging light. It should be explained herein: while the user operates the fundus camera 10 of the present invention, the processor 14 only partially and selectively activates one or more of the illumination elements 13IR and 13W according to the offset vector of the first lens group 11 with respect to the inspected eyeball EB. For example, the processor 14 looks up the direction and distance of the offset in a table to determine the positions and number of the illumination elements 13IR and 13W to be activated.

In one embodiment, according to the extraocular image output by the eyeball-offset detection device 12, the processor 14 may work out the size of the pupil of the inspected eyeball EB. Then, according to the offset vector of the first lens group 11 with respect to the inspected eyeball EB and the size of the pupil of the inspected eyeball EB, the processor 14 undertakes looking up in a table to selectively activate one or more of the illumination elements 13IR and 13W at corresponding positions. For example, it is preferred: the illumination lights generated by one or more activated illumination elements 13IR and 13W pass through the pupil of the inspected eyeball EB at the regions, which are far away from the central area of the pupil and far away from the imaging optical path. Thereby is decreased the probability of the ghost images generated by that the central area of the cornea reflects the illumination lights. In one embodiment, the annular illumination device 13 can be manually activated to turn on one or more illumination elements 13IR and 13W. For example, the illumination light is less likely to pass through some regions of the pupil of the testee suffering from cataract; in such a case, the illumination elements 13IR and 13W at specified positions may be manually activated to enhance the illumination on the fundus.

Refer to FIG. 5 again. The second lens group 15 is coaxially arranged in the second side of the first lens group 11. For example, the second lens group 15 is arranged in the hollow region of the annular illumination device 13. In one embodiment, the distance between the first lens group 11 and the annular illumination device 13 is smaller than or equal to the distance between the first lens group 11 and the second lens group 15. It is easily understood: in the condition that the second lens group 15 does not block the illumination lights generated by the annular illumination device 13, the arrangement that the distance between the first lens group 11 and the annular illumination device 13 may be slightly larger than the distance between the first lens group 11 and the second lens group 15 will not affect the operation of the present invention. It is easily understood: the second lens group 15 may include one or more lens modules, and each lens module may include one or more lenses. The technology of designing the imaging system is well known by the persons skilled in the art and will not repeat herein.

The image sensor 16 is arranged in the light exit side of the second lens group 15. The imaging light, which is reflected by the fundus of the inspected eyeball EB, passes the first lens group 11 and the second lens group 15 and converges on the image sensor 16 in sequence to form a fundus image of the inspected eyeball EB. The display device 17 is electrically connected with the image sensor 16 and displays the fundus image output by the image sensor 16.

Figure 8:
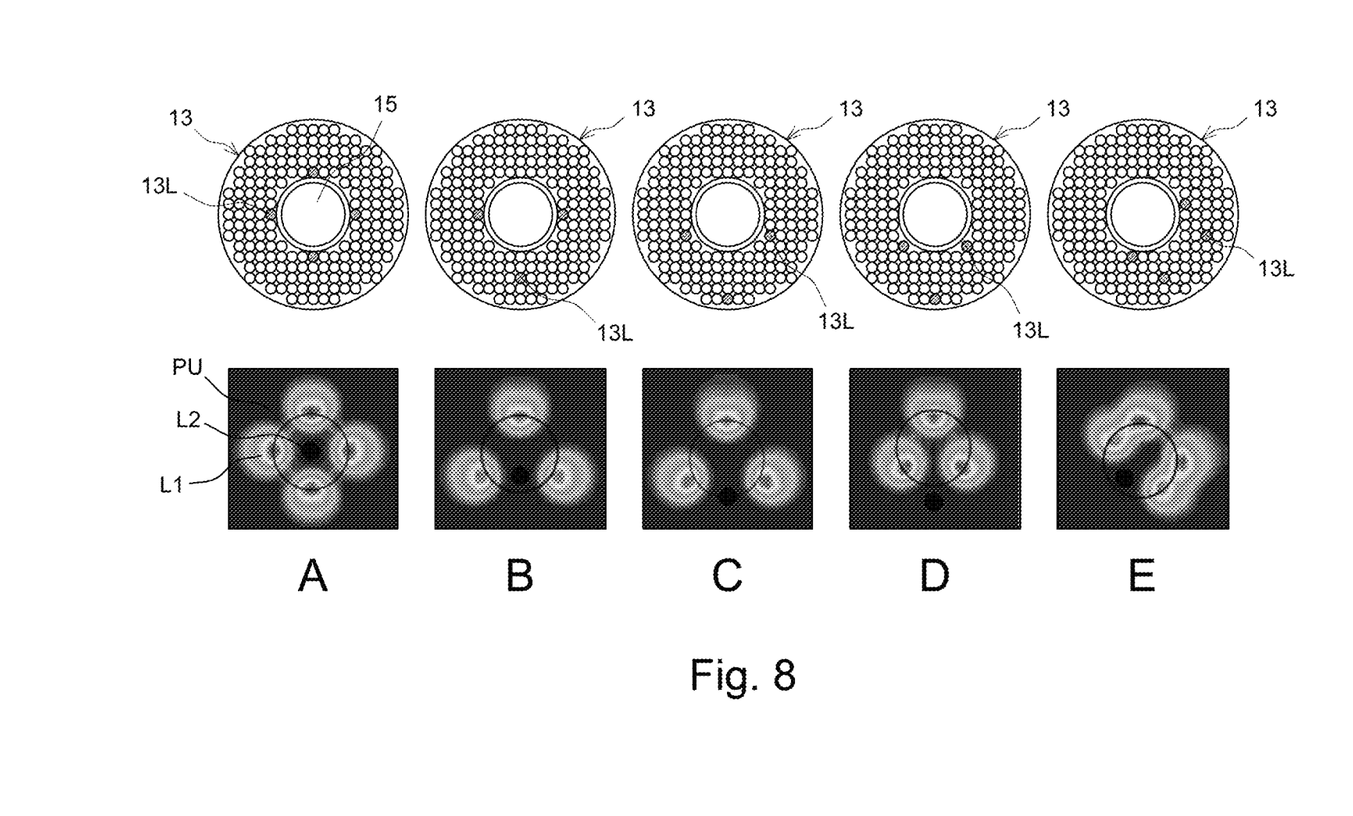
FIG. 8 is a diagram showing the results of the simulations of several activation modes of the annular illumination device according to embodiments of the present invention.

Refer to FIG. 8 for the simulation of several activation modes of the annular illumination device 13, which are corresponding to different offset vectors of the first lens group 11 with respect to the inspected eyeball EB, wherein a pupil with a 3.5 mm diameter is used in the simulation. The drawings in the top show the activation modes of the annular illumination device 13. The drawings in the bottom show the space relationships of the illumination optical paths L1, the imaging optical path L2, and the pupil PU of the inspected eyeball EB.

Refer to FIG. 8A. In the condition that the first lens group L1 is aligned to the inspected eyeball EB, four illumination elements 13L, which are respectively at the upper, lower, left and right regions of the annular illumination device 13, are activated. The illumination lights generated by the four illumination elements 13L are projected onto the perimeter of the pupil PU, i.e., far away from the central area of the pupil PU. Thus, the illumination optical paths L1 are separated from the imaging optical path L2 in space. Thereby, the best fundus images are obtained in the abovementioned condition.

Suppose that the first lens group 11 moves along the Y axis by 1 mm with respect to the inspected eyeball EB and that the activation mode in FIG. 8A is still used. Thus, the illumination light generated by the illumination element 13L in the upper region will be moved away from the pupil PU and unable to reach the fundus; the illumination light generated by the illumination element 13L in the lower region will be close to the central area of the pupil PU and causes significant ghost images. In order to solve the abovementioned problem, the annular illumination device 13 of the present invention activates three illumination elements 13L, as shown in FIG. 8B. Corresponding to the offset vector of the lens, the position of the activated illumination element 13L in the lower region also descends, whereby the illumination optical path L1 of the activated illumination element 13L is far away from the central area of the pupil PU, and whereby the probability of ghost images is decreased, and sufficient illumination is provided.

Suppose that the first lens group 11 moves along the Y axis by 2 mm with respect to the inspected eyeball EB. The three activated illumination elements 13L of the annular illumination device 13 are all moved downward, as shown in FIG. 8C. Thereby, the illumination optical paths L1 of all the activated illumination elements 13L are far away from the central area of the pupil PU. Thus, the probability of ghost images is decreased, and sufficient illumination is provided. It should be noted: while the first lens group 11 moves along the Y axis by 2 mm with respect to the inspected eyeball EB, a portion of the imaging optical path L2 is deviated from the pupil PU, and the imaging quality may be affected.

Suppose that the first lens group 11 moves along the Y axis by 2.5 mm with respect to the inspected eyeball EB. As shown in FIG. 8D, the annular illumination device 13 can still activate three illumination elements 13L at corresponding positions to make the illumination optical paths L1 thereof far away from the central area of the pupil PU, i.e., to keep the illumination optical paths L1 thereof appearing in the perimeter of the pupil PU. However, the imaging optical path L2 has been deviated from the pupil PU. Thus, the fundus camera is unlikely to acquire the fundus images in such a case. It is easily understood: the fundus camera of the present invention may still possibly obtain the fundus images if the inspected eyeball EB has a larger pupil, for example, the pupil has a diameter of 5 mm, or the pupil is enlarged by mydriatic.

Suppose that the first lens group 11 respectively moves along the Y axis and the X axis by 1 mm with respect to the inspected eyeball EB. As shown in FIG. 8E, the annular illumination device 13 can activate four illumination elements 13L at corresponding positions to make the illumination optical paths L1 thereof far away from the central area of the pupil PU and provide more uniform illumination.

From the above description, it is learned: according to the offset direction and offset distance of the lens with respect to the inspected eyeball, the fundus camera of the present invention can selectively activate the illumination elements at the corresponding positions of the annular illumination device to make the illumination optical paths far away from the central area of the pupil of the inspected eyeball and the imaging optical path so as to reduce the affection of the light reflected from the cornea and obtain better fundus images. In the present invention, it is preferred: further according to the size of the pupil of the inspected eyeball, the fundus camera selectively activate the illumination elements at the corresponding positions of the annular illumination device to make the illumination optical paths far away from the central area of the pupil of the inspected eyeball and the imaging optical path, whereby is further reduced the probability of ghost images caused by the light reflected from the cornea. Compared with the conventional fundus camera, the fundus camera of the present invention has a larger operable range and is able to obtain more acceptable fundus images. Briefly, no matter whether the operator who only experienced basic training operates the fundus camera of the present invention to align it to the inspected eyeball or the testee herself/himself moves the inspected eyeball to align it to the fundus camera of the present invention, the fundus camera of the present invention can always obtain acceptable fundus images.

In the embodiments shown in FIG. 6A and FIG. 7A, the annular illumination devices 13 respectively includes 180 and 120 illumination elements. In order to reduce the cost or simplify the control, the number of the illumination elements of the annular illumination device may be appropriately decreased, and the arrangement of the illumination elements may be modified, according to practical requirement. Alternatively, only activating a single illumination element according to the offset vector may also achieve the objective of the present invention. For example, the plurality of illumination elements arranged into a single circle (i.e., the distance between the optical axis O and each of the illumination element is the same) may also effectively decrease the probability of ghost images and enhance the illumination effect.

Figure 9:
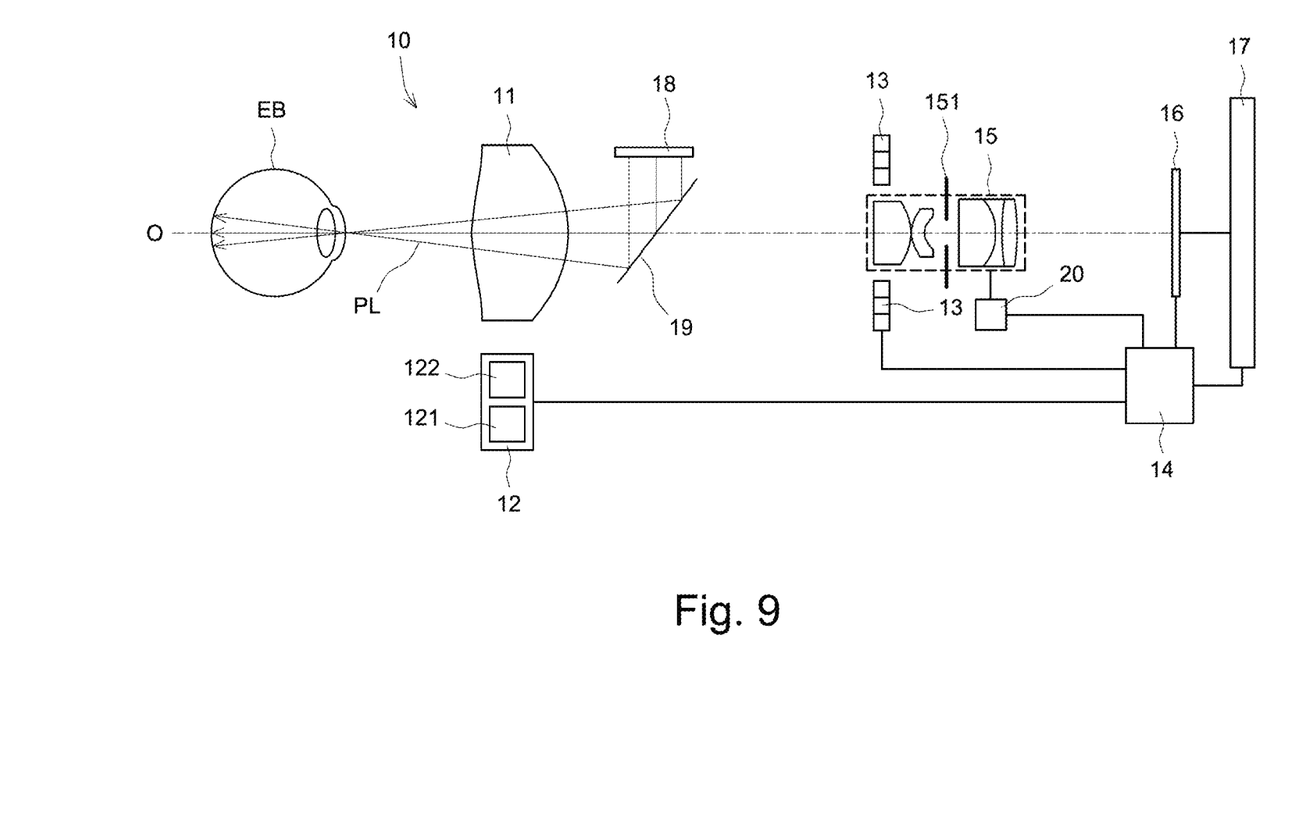
FIG. 9 is a diagram schematically showing a fundus camera according to another embodiment of the present invention.

Refer to FIG. 9. In one embodiment, the fundus camera of the present invention further comprises a light diaphragm 151, which is arranged inside the second lens group 15 to prevent the light reflected by the cornea of the inspected eyeball EB from entering the imaging system, whereby to promote the imaging quality. For example, while the pupil of the inspected eyeball EB is smaller, the size of the light beam of the imaging optical path may be decreased, whereby to increase the distance separating the illumination optical paths and the imaging optical path and decrease the probability that the unnecessary reflected light enters the imaging optical path. In one embodiment, the light diaphragm 151 is arranged between the lenses of the second lens group 15 or the light entrance side of the second lens group 15. The position of the light diaphragm 151 and the position of the pupil of the inspected eyeball EB are in object-image relations to each other, i.e., they are conjugate to each other. For example, the light diaphragm 151 is arranged in the light entrance side of the second lens group 15, and the light diaphragm 151 and the pupil of the inspected eyeball EB are conjugate to each other with respect to the first lens group 11. In one embodiment, the size of the aperture of the light diaphragm 151 is adjustable. For example, the size of the aperture of the light diaphragm 151 may be varied with different illumination conditions, different pupil sizes, or different working distances.

In one embodiment, the fundus camera of the present invention further comprises a fixation lamp 18, which is equivalently coaxially disposed in the optical axis O of the first lens group 11. For example, the fixation lamp 18 generates a precision light PL. The precision light PL is reflected by a light splitter 19, and then converged to the cornea of the inspected eyeball EB by the first lens group 11. After the reflection by the light splitter 19, the fixation lamp 15 is equivalently at the position of the intermediate image of the first lens group 11. Via the abovementioned structure, the precision light PL emitted by the fixation lamp 18 may be projected to the fundus of the inspected eyeball EB. The operator may fix the angle of the inspected eyeball EB via letting the testee watch the specified position lighted up by the fixation lamp 18. In the present invention, the design of the fixation lamp system is not limited by the abovementioned embodiment. For example, the fixation lamp system may include a relay lens and/or a focus adjuster. The technology to realize the fixation lamp system is well known by the persons skilled in the art and will not repeat herein.

In one embodiment, the fundus camera of the present invention further comprises a focus adjuster 20. The operator may use the focus adjuster 20 to image the fundus of the inspected eyeball EB on the image sensor 16. For example, the focus adjuster 20 may use a motor to drive at least one lens of the second lens group 15 to physically move along the optical axis O, whereby to adjust the focal length. In one embodiment, the second lens group 15 includes at least one liquid lens; the focus adjuster 20 may adjust the curvature of the liquid lens of the second lens group 15 to realize focal length adjustment. In one embodiment, the focus adjuster 20 may use appropriate mechanical structure to drive the image sensor 16 to physically move along the optical axis O, whereby to realize focal length adjustment.

In conclusion, the fundus camera of the present invention arranges a plurality of point-type light sources around the optical axis of the imaging system and selectively activates one or more point-type light sources at corresponding positions according to the offset vector of the lens with respect to the inspected eyeball and/or the size of the pupil of the inspected eyeball to make the illumination optical paths far away from the central area of the pupil of the inspected eyeball, whereby to reduce the affection of the light reflected from the cornea and upgrade the imaging quality. Hence, the fundus camera of the present invention has a larger operable range. In other words, although the lens is deviated from the inspected eyeball, the fundus camera of the present invention can still obtain acceptable fundus images.

The embodiments have been described above to demonstrate the technical thoughts and characteristics of the present invention to make the persons skilled in the art to understand, make, and use the present invention. However, these embodiments are not intended to limit the scope of the present invention. Any equivalent modification or variation according to the spirit of the present invention is to be also included by the scope of the present invention.

What is claimed is:

1. A fundus camera comprising:
a first lens group having a first side and a second side opposite to the first side, wherein the first side faces an inspected eyeball;
an eyeball-offset detection device detecting a relative position of the first lens group and the inspected eyeball;
an annular illumination device arranged in the second side of the first lens group and including a plurality of illumination elements arranged annularly, wherein an optical axis of the first lens group passes through a hollow region of the annular illumination device;
a processor electrically connected with the eyeball-offset detection device and the annular illumination device, working out an offset vector according to the relative position of the first lens group and the inspected eyeball, and selectively activating at least one of the plurality of illumination elements to generate an illumination light according to the offset vector, wherein the illumination light passes through the first lens group to a fundus of the inspected eyeball, and the fundus reflects the illumination light to form an imaging light;
a second lens group coaxially arranged in the second side of the first lens group;
an image sensor arranged in a light exit side of the second lens group, wherein the imaging light passes the first lens group and the second lens group and converges on the image sensor in sequence to form a fundus image; and
a display device electrically connected with the image sensor and displaying the fundus image formed in the image sensor.

2. The fundus camera according to claim 1, wherein the plurality of illumination elements is arranged in arrays, radiately, or alternately with the optical axis of the first lens group being a center.

3. The fundus camera according to claim 1, wherein a distance between the first lens group and the annular illumination device is smaller than or equal to a distance between the first lens group and the second lens group.

4. The fundus camera according to claim 1, wherein the processor activates more than one of the plurality of illumination elements.

5. The fundus camera according to claim 1, wherein the illumination elements are point-type illumination elements.

6. The fundus camera according to claim 1, wherein the plurality of illumination elements includes a plurality of infrared light LEDs and a plurality of white light LEDs.

7. The fundus camera according to claim 1, wherein the plurality of illumination elements includes a plurality of infrared light LEDs and a plurality of visible light LEDs emitting visible lights of different wavelength bands.

8. The fundus camera according to claim 1, wherein the illumination light generated by at least one of the plurality of illumination elements passes through a pupil of the inspected eyeball at a location far away from a central area of the pupil.

9. The fundus camera according to claim 1, wherein at least one of the plurality of the illumination elements of the annular illumination device is manually and selectively activated.

10. The fundus camera according to claim 1, wherein the eyeball-offset detection device includes an extraocular image sensor electrically connected with the processor and capturing extraocular images of the inspected eyeball; the processor works out the offset vector according to the extraocular images.

11. The fundus camera according to claim 10, wherein the processor works out a size of a pupil of the inspected eyeball according to the extraocular images; the processor selectively activates at least one of the plurality of illumination elements to generate the illumination light according to the offset vector and the size of the pupil.

12. The fundus camera according to claim 10, wherein the eyeball-offset detection device includes a reference illumination element, which generates a reference light to irradiate on the inspected eyeball; the reference light is reflected by a cornea of the inspected eyeball to form a reference light spot on the extraocular images; according to a reference position of the reference light spot and the extraocular image, the processor work out the offset vector.

13. The fundus camera according to claim 12, wherein the reference light is an invisible light.

14. The fundus camera according to claim 1, wherein the eyeball-offset detection device comprises a stereo camera.

15. The fundus camera according to claim 1 further comprising:
a focus adjuster physically moving the image sensor or at least one lens of the second lens group, or adjusting a curvature of a liquid lens of the second lens group to image the fundus on the image sensor.

16. The fundus camera according to claim 1 further comprising:
a light diaphragm arranged inside the second lens group.

17. The fundus camera according to claim 16, wherein a size of an aperture of the light diaphragm is adjustable.

18. The fundus camera according to claim 1 further comprising:

a fixation lamp equivalently coaxially arranged in the optical axis of the first lens group.

* * * * *